United States Patent [19]

Pollitzer et al.

[11] 4,069,269

[45] Jan. 17, 1978

[54] ISOMERIZATION OF NAPHTHENES

[75] Inventors: Ernest L. Pollitzer, Skokie; John C. Hayes, Palatine, both of Ill.

[73] Assignee: UOP Inc., Des Plaines, Ill.

[21] Appl. No.: 737,353

[22] Filed: Nov. 1, 1976

Related U.S. Application Data

[60] Division of Ser. No. 633,889, Nov. 20, 1975, Pat. No. 4,013,738, which is a continuation-in-part of Ser. No. 522,209, Nov. 8, 1974, Pat. No. 3,960,710.

[51] Int. Cl.$^2$ .............................................. C07C 13/08
[52] U.S. Cl. ............................. 260/666 P; 260/666 R; 252/441; 252/442
[58] Field of Search ....................... 260/666 P, 666 R; 252/441, 442

[56] References Cited

U.S. PATENT DOCUMENTS

| 3,630,961 | 12/1971 | Wilhelm | 260/666 P |
|---|---|---|---|
| 3,903,195 | 9/1975 | Franck et al. | 260/666 P |

*Primary Examiner*—Veronica O'Keefe
*Attorney, Agent, or Firm*—James R. Hoatson, Jr.; Thomas K. McBride; William H. Page, II

[57] ABSTRACT

Isomerizable hydrocarbons are isomerized using a catalyst comprising a combination of a platinum group component, a cobalt component, a tin component and a halogen component with a porous carrier material. The cobalt and platinum group components are reduced to the metallic state while the tin is present in a positive oxidation state.

15 Claims, No Drawings

ISOMERIZATION OF NAPHTHENES

CROSS-REFERENCE TO RELATED APPLICATIONS

This application is a division of our co-pending application Ser. No. 633,889 filed Nov. 20, 1975 now U.S. Pat. No. 4,013,738 which is a continuation-in-part of our application Ser. No. 522,209 filed Nov. 8, 1974, now U.S. Pat. No. 3,959,988 the teachings of which are incorporated herein by specific reference thereto.

FIELD OF THE INVENTION

This invention relates to a catalyst and process for isomerizing isomerizable hydrocarbons including isomerizable paraffins, cycloparaffins, olefins and alkylaromatics. More particularly, this invention relates to a process for isomerizing hydrocarbons with a catalyst comprising a combination of a platinum group component, a cobalt component, a tin component and a halogen component with a porous carrier material. The present invention uses a dual-function catalyst having both a hydrogenation-dehydrogenation function and a cracking function which affords substantial improvements in hydrocarbon isomerization processes that have traditionally used dual-function catalysts.

Processes for the isomerization of hydrocarbons have acquired significant importance within the petrochemical and petroleum refining industry. The demand for para-xylene has created a demand for processes to isomerize other xylene isomers and ethylbenzene to produce para-xylene. The demand for certain branched chain paraffins, such as isobutane or isopentane, as intermediates in producing high octane motor fuel alkylate, can be met by isomerizing the corresponding normal paraffins. It is desired that the alkylate be highly branched to provide a high octane rating. This can be accomplished by alkylating an isoparaffin with $C_4$–$C_7$ internal olefins which, in turn, can be produced by isomerization of corresponding linear alpha-olefins.

Catalytic composites exhibiting a dual hydrogenation-dehydrogenation and cracking function are widely used in the petroleum and petrochemical industry to isomerize hydrocarbons. Such catalysts generally have a heavy metal component e.g., metals or metallic compounds of Group V through VIII of the Periodic Table, to impart a hydrogenation-dehydrogenation function, with an acid-acting inorganic oxide to impart a cracking function. In catalysis of isomerization reactions, it is important that the catalytic composite not only catalyze the specific desired isomerization reaction by having its dual hydrogenation-dehydrogenation function correctly balanced against its cracking function, but also that the catalyst perform its desired functions well over prolonged periods of time.

The performance of a given catalyst in a hydrocarbon isomerization process is typically measured by the activity, selectivity, and stability of the catalyst. Activity refers to the ability of a catalyst to isomerize the hydrocarbon reactants into the corresponding isomers at a specified set of reaction conditions; selectivity refers to the percent of reactants isomerized to form the desired isomerized product and/or products; stability refers to the rate of change of the selectivity and activity of the catalyst.

The principal cause of instability (i.e., loss of selectivity and activity in an originally selective, active catalyst) is the formation of coke on the catalytic surface of the catalyst during the reaction. This coke is characterizable as a high molecular weight, hydrogen-deficient, carbonaceous material, typically having an atomic carbon to hydrogen ratio of about 1 or more. Thus, a problem in the hydrocarbon isomerization art is the development of more active and selective composites not sensitive to the carbonaceous materials and/or having the ability to suppress the rate of formation of these carbonaceous materials on the catalyst. A primary aim of the art is to develop a hydrocarbon isomerization process utilizing a dual-function catalyst having superior activity, selectivity and stability. In particular, it is desired to provide a process wherein hydrocarbons are isomerized without excess cracking or other decomposition reactions which lower the overall yield of the process and make it more difficult to operate.

SUMMARY OF THE INVENTION

It is an object of this invention to provide a process for isomerizing isomerizable hydrocarbons. It is another object of this invention to provide an isomerization process using a particular isomerization catalyst effective in isomerizing isomerizable hydrocarbons without introducing undesired decomposition and/or cracking reactions. It is a further object of this invention to provide a process for isomerizing isomerizable hydrocarbons utilizing a dual-function catalyst having superior activity, selectivity and stability.

It is also an object of the present invention to provide an improved isomerization catalyst.

Accordingly, the present invention provides a catalyst comprising a porous carrier material containing, on an elemental basis, 0.01 to 2 wt. % platinum group metal, 0.1 to 5 wt. % cobalt, 0.01 to 5 wt. % tin and 0.1 to 10 wt. % halogen, and about 1 to 100 wt. % of a Friedel-Crafts metal halide calculated on a Friedel-Crafts metal halide free basis, wherein the platinum group metal cobalt and tin are uniformly dispersed throughout the porous carrier material, wherein substantially all of the platinum group metal and cobalt are present in the elemental metalic state and substantially all of the tin is present in an oxidation state above that of the elemental metal.

In another embodiment, the present invention provides a process for isomerizing an isomerizable hydrocarbon which comprises contacting said hydrocarbon at isomerization conditions with a catalyst comprising a porous carrier material containing, on an elemental basis, 0.01 to 2 wt. % platinum group metal, 0.1 to 5 wt. % cobalt, 0.01 to 5 wt. % tin and 0.1 to 10 wt. % halogen, wherein substantially all of the platinum group metal, cobalt and tin are uniformly dispersed throughout the porous carrier material, wherein substantially all of the platinum group metal and cobalt are present in the elemental metallic state and wherein substantially all of the tin is present in an oxidation state above that of the elemental metal.

DETAILED DESCRIPTION

The process of this invention is applicable to the isomerization of isomerizable saturated hydrocarbons including acyclic paraffins and naphthenes and is particularly suitable for the isomerization of straight chain or mildly branched chain paraffins containing 4 or more carbon atoms per molecule such as normal butane, normal pentane, normal hexane, normal heptane, normal octane, etc., and mixtures thereof. Cycloparaffins applicable are those containing at least 5 carbon atoms in the ring such as alkylcyclopentanes and cyclohexanes, including methylcyclopentane, dimethylcyclopentane, cyclohexane, methylcyclohexane, dimethylcyclohexane, etc. This process also applies to the conversion of mixtures of paraffins and/or naphthenes such as those derived by selective fractionation and distillation of straight-run natural gasolines and naphthas. Such mixtures of paraffins and/or naphthenes include the so-called pentane fractions, hexane fractions and mixtures thereof. It is not intended, however, to limit this invention to these enumerated saturated hydrocarbons and it is contemplated that straight or branched chain saturated hydrocarbons and naphthenes containing up to about 20 carbon atoms per molecule may be isomerized according to the process of the present invention with $C_4$–$C_9$ acyclic saturated hydrocarbons and $C_5$–$C_9$ cycloparaffins being particularly preferred.

The olefins applicable within this isomerization process are generally a mixture of olefinic hydrocarbons of approximately the same molecular weight, including the 1-isomer, 2-isomer and other position isomers, capable of undergoing isomerization to an olefin in which the double bond occupies a different position in the hydrocarbon chain. The process of this invention can be used to provide an olefinic feedstock for motor fuel alkylation purposes containing an optimum amount of the more centrally located double bond isomers, by converting the 1-isomer, or other near-terminal-position isomer into olefins wherein the double bond is more centrally located in the carbon atoms chain. The process of this invention is applicable to the isomerization of such isomerizable olefinic hydrocarbons as 1-butene to 2-butene or 3-methyl-1-butene to 2-methyl-2-butene. The process of this invention can be utilized to shift the double bond of an olefinic hydrocarbon such as 1-pentene, 1-hexene, 2-hexene, or 4-methyl-1-pentane to a more centrally located position so that 2-pentene, 2-hexene, 3-hexene or 4-methyl-2-pentene, respectively, can be obtained. It is not intended to limit this invention to the enumerated olefinic hydrocarbons. It is contemplated that shifting the double bond to a different position may be effective in straight or branched chain olefinic hydrocarbons containing from 4 up to about 20 carbon atoms per molecule. The process of this invention also applies to the hydroisomerization of olefins wherein olefins are converted to branched-chain paraffins and/or branched olefins.

The process of this invention is also applicable to the isomerization of isomerizable alkylaromatic hydrocarbons, e.g., ortho-xylene, meta-xylene, para-xylene, ethylbenzene, the ethyltoluenes, the trimethylbenzenes, the diethylbenzenes, the triethylbenzenes, normal propylbenzene, isopropylbenzene, etc., and mixtures thereof. Preferred isomerizable alkylaromatic hydrocarbons are the alkylbenzene hydrocarbons, particularly the $C_8$ alkylbenzenes, and non-equilibrium mixtures of various $C_8$ aromatic isomers. Higher molecular weight alkylaromatic hydrocarbons such as the alkylnaphthalenes, the alkylanthracenes, the alkylphenanthrenes, etc., are also suitable.

The isomerizable hydrocarbons may be utilized as found in selective fractions from various naturally-occurring petroleum streams, e.g., as individual components or as certain boiling range fractions obtained by the selective fractionation and distillation of catalytically cracked gas oil. The process of this invention may be utilized for complete conversion of isomerizable hydrocarbons when they are present in minor quantities in various fluid or gaseous streams. The isomerizable hydrocarbons for use in the process of this invention need not be concentrated. For example, isomerizable hydrocarbons appear in minor quantities in various refinery offstreams, usually diluted with gases such as hydrogen, nitrogen, methane, ethane, propane, etc. These offstreams, containing minor quantities of isomerizable hydrocarbons, are obtained from various refinery installations, including thermal cracking units, catalytic cracking units, thermal reforming units, coking units, polymerization units, dehydrogenation units, etc., and have in the past been burned as fuel, since an economical process for the utilization of the hydrocarbon content has not been available. This is particularly true of refinery fluid streams which contain minor quantities of isomerizable hydrocarbons. The process of this invention allows the isomerization of aromatic streams such as reformate to produce xylenes, particularly para-xylene, thus upgrading the reformate from its gasoline value to a high petrochemical value.

As hereinbefore indicated, the catalyst utilized in the process of the present invention comprises a porous carrier material or support having combined therewith catalytically effective amounts of a platinum group component, a cobalt component, a tin component, and a halogen component with a porous carrier material.

Considering first the porous carrier material utilized in the present invention, it is preferred that the material be a porous, adsorptive, high-surface area support having a surface area of about 25 to about 500 m²/g. The porous carrier material should be relatively refractory to the conditions utilized in the isomerization process, and it is intended to include within the scope of the present invention carrier materials which have traditionally been utilized in dual-function hydrocarbon conversion catalysts such as: (1) activated carbon, coke or charcoal; (2) silica or silica gel, silicon carbide, clays and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractor inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$ and other like compounds having the formula $MO \cdot Al_2O_3$, where M is a metal having a valence of 2; and, (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in some embodiments the alumina carrier material may contain minor proportion of other well known refractory inorganic oxides such as silica, zirconia, magnesia, etc.; however, the preferred support is substantially pure gamma- or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 m²/g. In general, best results are typically obtained with a gamma-alumina carrier material which is used in the form of spherical particles having: a relatively small diameter (i.e., typically about 1/16 inch), an apparent bulk density of about 0.3 to about 0.8 g/cc, a pore volume of about 0.4 ml/g and a surface area of about 200 m²/g.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

One essential constituent of the improved trimetallic composite used in the present invention is a tin component, and it is an essential feature of the present invention that substantially all of the tin component in the composite is in an oxidation state above that of the elemental metal. That is, it is believed that best results are obtained when substantially all of the tin component exists in the catalytic composite in the +2 or +4 oxidation state. Accordingly, the tin component will be present in the composite as a chemical compound such as the oxide, sulfide, halide, oxyhalide, oxysulfide and the like, wherein the tin moiety is in a positive oxidation state, or in chemical combination with the carrier material in a manner such that the tin component is in a positive oxidation state. Controlled reduction experiments with the catalytic composites produced by the preferred methods of preparing the instant catalytic composite have established that the tin component in these catalysts is in a positive oxidation state and is not reduced by contact with hydrogen at temperatures in the range of 1000° to 1200° F. It is important to note that this limitation on the oxidation state of the tin component requires extreme care in preparation and use of the present catalyst to insure that it is not subjected to a reducing atmosphere at temperatures above 1200° F. Equally significant is our observation that it is only when the tin component is in a uniformly dispersed state in the carrier material that it has the capability to maintain its positive oxidation state when subjected to hereinafter described prereduction step. Stated another way, if the tin component is not properly dispersed on the support it can be reduced in the prereduction step and result in an inferior catalyst. Based on the evidence currently available it is believed that best results are obtained when the tin component is present in the catalyst as tin oxide. The term "tin oxide" as used herein refers to a coordinated tin-oxygen complex which is not necessarily stoichiometric.

Interrelated with this oxidation state limitation are the factors of dispersion of the tin component in the support and of particle size of the tin component. This interrelationship emanates from the observation that it is only when the tin component is uniformly dispersed throughout the carrier material in a particle having a maximum chord length less than 100 Angstroms that it can successfully maintain its preferred oxidation state when it is subjected to a high temperature prereduction treatment as hereinafter described. Thus in a preferred embodiment of our invention, the instant multimetallic catalytic composite is prepared in a manner selected to meet the stated particle size and uniform dispersion limitations. By the use of the expression "uniform dispersion of the tin component in the carrier material" it is intended to describe the situation where the concentration of the tin ingredient is approximately the same in any reasonably divisable portion of the carrier material. Similarly, the expression "particles having a maximum chord length less than 100 Angstroms" is intended to denote particles that would pass through a sieve having a 100 Angstrom mesh size if it were possible to make such a sieve.

The tin component may be incorporated into the catalytic composite in any suitable manner known to effectively disperse this component throughout the carrier material in the required particle size. Thus this component may be added to the carrier by coprecipitation or cogellation of a suitable soluble tin salt with the carrier material, by ion-exchange of suitable tin ions with ions contained in the carrier material when the ion exchange sites are uniformly distributed throughout the carrier or controlled impregnation of the carrier material with a suitable soluble tin salt under conditions selected to result in penetration of all sections of the carrier material by the tin component. One preferred method of incorporating the tin component involves coprecipitating it during the preparation of the preferred carrier material, alumina. This method typically involves the addition of a suitable soluble tin compound such as stannous or stannic chloride to an alumina hydrosol, mixing these ingredients to obtain a uniform distribution of the tin moiety throughout the sol and then combining the hydrosol with a suitable gelling agent and dropping the resulting mixture into an oil bath, etc., as explained in detail hereinbefore. After drying and calcining the resulting gelled carrier material there is obtained an intimate combination of alumina and tin oxide having the required dispersion and particle size. Another preferred method of incorporating the tin component into the catalytic composite involves utilization of a soluble, decomposable compound of tin to impregnate the porous carrier material. In general, the solvent used in this impregnation step is selected on the basis of the capability to dissolve the desired tin compound and to hold the tin moiety in solution until it is evenly distributed throughout the carrier material and is preferably an aqueous, rather strongly acidic solution. Thus the tin component may be added to the carrier material by commingling the latter with an aqueous solution of a suitable tin salt or suitable compound of tin such as stannous bromide, stannous chloride, stannic chloride, stannic chloride pentahydrate, stannic chloride diamine, stannic trichloride bromide, stannic chromate, stannous fluoride, stannic fluoride, stannic iodide, stannic sulfate, stannic tartrate and the like compounds. The acid used in the impregnation solution may be any organic or inorganic acid that is capable of maintaining the pH of the impregnation solution in the range of about −1 or less to about 3 and preferably less than 1 during the impregnation step and that does not contaminate the resultant catalyst. Suitable acids are: inorganic acids such as hydrochloric acid, nitric acid and the like; and strongly acidic organic acids such as oxalic acid, malonic acid, citric acid and the like. A particularly preferred impregnation solution comprises stannic or stannous chloride dissolved in a hydrochloric acid solution containing HCl in an amount corresponding to at least about 5 weight percent of the carrier material which is to be impregnated. Another useful impregnation solution is stannous or stannic chloride dissolved in an anhydrous alcohol such as ethanol. In general, the tin component can be incorporated either prior to, simultaneously with, or after the other metallic components are added to the carrier material. However, we have found that excellent results are obtained when the tin component is incorporated simultaneously with the platinum group component and cobalt component.

Regardless of which tin compound is used in the preferred impregnation step, it is essential that the tin component be uniformly distributed throughout the carrier material. In order to achieve this objective with an aqueous impregnation solution it is necessary to dilute the impregnation solution to a volume which is approximately equal to or substantially in excess of the void volume of the carrier material which is impregnated and to add a relatively strong acid such as hydrochloric acid, nitric acid and the like to the impregnation solution in an amount calculated to maintain the pH of the impregnation solution in a range of about −1 or less to about 3, preferably less than 1. It is preferred to use a volume ratio of impregnation solution to carrier material of at least 0.5:1 and preferably about 1:1 to about 10:1 or more. Similarly, it is preferred to use a relatively long contact time during the impregnation step ranging from about one-fourth hour up to about one-half hour or more drying to remove excess solvent in order to insure a high dispersion of the tin component into the carrier material. The carrier material is, likewise, preferably constantly agitated during this preferred impregnation step.

Regarding the amount of the tin component contained in the instant composite, it is preferably sufficient to constitute about 0.01 to about 5 weight percent of the final composite, calculated on an elemental basis, although substantially higher amounts of tin may be utilized in some cases. Best results are typically obtained with about 0.1 to about 1 weight percent tin.

A second essential ingredient of the subject catalyst is the platinum group component, i.e., platinum, iridium, osmium, ruthenium, rhodium, palladium or mixtures thereof as a second component of the present composite. It is an essential feature of the present invention that substantially all of this platinum group component exists within the final catalytic composite in the elemental metallic state. Generally, the amount of this component present in the final catalytic composite is small compared to the qualities of the other components combined therewith. In fact, the platinum group component generally will comprise about 0.01 to about 2 weight percent of the final catalytic composite, calculated on an elemental basis. Excellent results are obtained when the catalyst contains about 0.05 to about 1 weight percent of platinum or palladium metal.

This platinum group component may be incorporated in the catalytic composite in any suitable manner known to result in a relatively uniform distribution of this component in the carrier material such as coprecipitation or cogellation, ion exchange or impregnation. The preferred method of preparing the catalyst involves the utilization of a soluble, decomposable compound of platinum or palladium to impregnate the carrier material in a relatively uniform manner. For example, this component may be added to the support by commingling the latter with an aqueous solution of chloroplatinic or chloropalladic acid. Other water-soluble platinum group compounds which may be used include chloriridic acid, rhodium trichloride, ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diammine palladium (II) hydroxide, tetrammine palladium (II) chloride, etc. The utilization of a platinum or palladium chloride compound, such as chloroplatinic or chloropalladic acid, is preferred since it facilitates the incorporation of both the platinum or palladium component and at least a minor quantity of the halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum group compounds; however, in some cases it may be advantageous to impregnate the carrier material when it is in a gelled state.

Yet another essential ingredient of the present catalytic composite is a cobalt component. Although this component may be initially incorporated into the composite in many different decomposable forms which are hereinafter stated, our basic finding is that the catalytically active state for hydrocarbon conversion with this component is the elemental metallic state. Consequently, it is a feature of our invention that substantially all of the cobalt component exists in the catalytic composite either in the elemental metallic state or in a state which is reducible to the elemental state under hydrocarbon conversion conditions. Examples of this last state are obtained when the cobalt component is initially present in the form of cobalt oxide, halide, oxyhalide, and the like reducible compounds. As a corollary to this basic finding on the active state of the cobalt component, it follows that the presence of cobalt in forms which are not reducible at hydrocarbon conversion conditions is to be scrupulously avoided if the full benefits of the present invention are to be realized. Illustrative of these undesired forms are cobalt sulphide and the cobalt oxysulphur compounds such as cobalt sulphate. Best results are obtained when the composite initially contains all of the cobalt component in the elemental metallic state or in a reducible oxide state or in a mixture of these states. All available evidence indicates that the preferred preparation procedure specifically described in Example I results in a catalyst having the cobalt component in a reducible oxide form.

The cobalt component may be incorporated into the catalytic composite in any suitable manner known to those skilled in the catalyst formulation art to result in a relatively uniform distribution of cobalt in the carrier material such as coprecipitation cogellation, ion-exchange, impregnation, etc. In addition, it may be added at any stage of the preparation of the composite — either during preparation of the carrier material or thereafter — since the precise method of incorporation used is not deemed to be critical. However, best results are obtained when the cobalt component is relatively uniformly distributed throughout the carrier material in a relatively small particle or crystallite size having a maximum dimension of less than 100 Angstroms, and the preferred procedures are the ones that are known to result in a composite having a relatively uniform distribution of the cobalt moiety in a relatively small particle size. One acceptable procedure for incorporating this component into the composite involves cogelling or coprecipitating the cobalt component during the preparation of the preferred carrier material, alumina. This procedure usually comprehends the addition of a soluble, decomposable, and reducible compound of cobalt such as cobalt chloride or nitrate to the alumina hydrosol before it is gelled. The resulting mixture is then finished by conventional gelling, aging, drying and calcination steps as explained hereinbefore. One preferred way of incorporating this component is an impregnation step wherein the porous carrier material is impregnated with a suitable cobalt-containing solution either before, during or after the carrier material is calcined or oxidized. The solvent used to form the impregnation solution may be water, alcohol, ether or any other suitable organic or inorganic solvent provided the solvent does not adversely interact with any of the other ingredients of the composite or interfere with the distribution and reduction of the cobalt component. Preferred impregnation solutions are aqueous solutions of water-soluble, decomposable, and reducible cobalt compounds. Best results are ordinarily obtained when the impregnation solution is an aqueous solution of cobalt chloride or cobalt nitrate. This cobalt component can be added to the carrier material, either prior to, simultaneously with, or after the other metallic components are combined therewith. Best results are usually achieved when this component is added simultaneously with the platinum group component via an acidic aqueous impregnation solution.

The cobalt component should comprise, on an elemental basis, about 0.1 to 5 weight percent of the finished catalyst, and preferably about 0.5 to 2 weight percent.

It is essential to incorporate a halogen component into the trimetallic catalytic composite of the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g., as the chloride). This combined halogen may be either fluorine, chlorine, iodine, bromine, or mixtures thereof. Of these, fluorine and particularly chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum group metal and cobalt components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. The halogen will be typically combined with the carrier material in an amount sufficient to result in a final composite that contains about 0.1 to about 10% and preferably about 1 to about 5%, by weight, or halogen, calculated on an elemental basis. It is to be understood that the specified level of halogen component in the instant catalyst can be achieved or maintained during use in the present isomerization process by continuously or periodically adding to the reaction zone a decomposable halogen-containing compound such as an organic chloride (e.g., ethylene dichloride, carbon tetrachloride, t-butyl chloride) in an amount of about 1 to 100 wt. ppm. of the hydrocarbon feed, and preferably about 1 to 10 wt. ppm.

Regarding the preferred amounts of the various metallic components of the subject catalyst, we have found it to be a good practice to specify the amounts of the cobalt component and the tin component as a function of the amount of the platinum group metal component. On this basis, the amount of the cobalt component is ordinarily selected so that the atomic ratio of cobalt to platinum group metal contained in the composite is about 0.8:1 to 66:1 with the preferred range being about 1.6:1 to 18:1. Similarly, the amount of tin component is ordinarily selected to produce a composite containing an atomic ratio of tin to platinum group metal of about 0.1:1 to about 13:1, with the preferred range being about 0.3:1 to about 5:1.

Another significant parameter for the instant catalyst is the "total metals content" which is defined to be the sum of the platinum group component, the cobalt component and the tin component, calculated on an elemental basis. Good results are ordinarily obtained with the subject catalyst when this parameter is fixed at a value of about 0.15 to about 5 weight percent, with best results ordinarily achieved at a metals loading of about 0.3 to about 3 weight percent.

Regardless of the details of how the components of the catalyst are combined with the porous carrier material, the final catalyst generally will be dried at a temperature of about 90° to about 310° C for a period of at least about 2 to about 24 hours or more, and finally calcined or oxidized at a temperature of about 375° to about 600° C in an air or oxygen atmosphere for a period of about 0.5 to about 10 hours in order to convert substantially all of the metallic components substantially to the oxide form. Because a halogen component is utilized in the catalyst, best results are generally obtained when the halogen content of the catalyst is adjusted during the calcination step by including a halogen or a halogen-containing compound such as HCl in the air or oxygen atmosphere utilized. In particular, when the halogen component of the catalyst is chlorine, it is preferred to use a mole ratio of water to hydrogen chloride of about 5:1 to about 100:1 during at least a portion of the calcination step in order to adjust the final chlorine content of the catalyst to a range of about 0.1 to about 10 weight percent.

An optional ingredient for the trimetallic catalyst of the present invention is a Friedel-Crafts metal halide component. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this optional ingredient can be incorporated into the composite of the present invention by way of the conventional methods for adding metallic halides of this type; however, best results are ordinarily obtained when the metallic halide is sublimed onto the surface of the carrier material according to the preferred method disclosed in U.S. Pat. No. 2,999,074, which is incorporated by reference.

In the preferred method, wherein the calcined composite is impregnated with a Friedel-Crafts metal halide component, the presence of chemically combined hydroxyl groups in the refractory inorganic oxide allows a reaction to occur between the Friedel-Crafts metal halide and the hydroxy group of the carrier material. For example, aluminum chloride reacts with the hydroxyl groups of the preferred alumina carrier material to yield Al-O-AlCl$_2$ active centers which enhance the catalytic behavior of the composite. Since chloride ions and hydroxyl ions occupy similar sites on the carrier surface more hydroxyl sites will be available for possible interaction with the Friedel-Crafts metal halide when the chloride population of the carrier sites is low. Therefore, potentially more active Friedel-Crafts type versions of the catalyst will be obtained when the chloride content of the carrier material is in the low range of the 0.1 to 10 weight range. Some halogen must be present on the carrier material at all times, however, to maintain proper dispersion of the other active elements.

The Friedel-Crafts metal halide may be impregnated onto the calcined composite containing combined hydroxyl groups by the sublimation of the Friedel-Crafts metal halide onto the calcined composite under conditions such that the sublimed Friedel-Crafts metal halide is combined with the hydroxyl groups of the calcined composite. This reaction is typically accompanied by the elimination of about 0.5 to about 2.0 moles of hydrogen chloride per mole of Friedel-Crafts metal halide reacted with the carrier material. For example, in the case of subliming aluminum chloride, which sublimes at about 184° C, suitable impregnation temperatures range from about 190° C to about 700° C, with a preferable range being between about 200° C and about 600° C. The sublimation can be conducted at atmospheric pressure or under increased pressure and in the presence of diluent gases such as hydrogen or light paraffinic hydrocarbons or both. The impregnation of the Friedel-Crafts metal halide may be conducted batch wise, but a preferred method for impregnating the calcined composite is to pass sublimed AlCl$_3$ vapors, in admixture with a carrier gas such as hydrogen, through a calcined catalyst bed. This method both continuously deposits and reacts the aluminum chloride and also removes the evolved HCl.

The amount of Friedel-Crafts metal halide combined with the calcined composite may range from about 1 weight percent up to about 100 weight percent of the Friedel-Crafts metal halide-free, calcined composite. The final composite containing the sublimed Friedel-Crafts metal halide is treated to remove the unreacted Friedel-Crafts metal halide by subjecting the composite to a temperature above the sublimation temperature of the Friedel-Crafts metal halide for a time sufficient to remove from the composite any unreacted Friedel-Crafts metal halide. In the case of AlCl$_3$, temperatures of about 400° C to about 600° C, and times of from about 1 to about 48 hours are sufficient.

In a preferred embodiment of the present invention, the resultant oxidized catalytic composite is subjected to a substantially water-free and hydrocarbon-free reduction step prior to its use in the conversion of hydrocarbons. This step is designed to selectively reduce the platinum or palladium and cobalt components to the corresponding metals and to insure a uniform and finely divided dispersion of these metallic components throughout the carrier material, while maintaining the tin component in a positive oxidation state. Preferably substantially pure and dry hydrogen (i.e., less than 20 vol. ppm. H$_2$O) is used as the reducing agent in this step. The reducing agent is contacted with the oxidized catalyst at conditions including a temperature of about 425° C to about 650° C and a period of time of about 0.5 to 2 hours to reduce substantially all of the platinum or palladium and cobalt components to their elemental metallic state while maintaining the tin component in an oxidation state above that of the elemental metal. This reduction treatment may be performed in situ as part of a start-up sequence if precautions are taken to predry the plant to a substantially water-free state and if substantially water-free and hydrocarbon-free hydrogen is used.

As used herein, the expression cobalt component is intended to mean the portion of the cobalt component that is available for use in accelerating the particular hydrocarbon conversion reaction of interest. For certain types of carrier materials which can be used in the preparation of the instant catalytic composite, it has been observed that a portion of the cobalt incorporated therein is essentially bound-up in the crystal structure thereof in a manner which essentially makes it more a part of the refractory carrier material than a catalytically active component. Specific examples of this effect are observed when the carrier material can form a spinel or spinel-like structure with a portion of the cobalt component. When this effect occurs, it is only with great difficulty that the portion of the cobalt bound-up with the support can be reduced to a catalytically active state and the conditions required to do this are beyond the severity levels normally associated with hydrocarbon conversion conditions and are in fact likely to seriously damage the necessary porous characteristics of the support. In the cases where cobalt can interact with the crystal structure of the support to render a portion thereof catalytically unavailable, the concept of the present invention merely requires that the amount of cobalt added to the subject catalyst be adjusted to satisfy the requirements of the support as well as the catalytically available cobalt requirements of the present invention. Against this background then, the hereinbefore stated specifications for oxidation state and dispersion of the cobalt component are to be interpreted as directed to a description of the catalytically availble cobalt. On the other hand, the specifications for the amount of cobalt used are to be interpreted to include all of the cobalt contained in the catalyst in any form.

The resulting reduced catalytic composite is preferably maintained in a sulfur-free state during its preparation and use. The beneficial interaction of the catalytically available cobalt component with the other ingredients of the catalyst is contingent upon the maintenance of the cobalt in a highly dispersed, readily reducible state in the carrier material. Surfur in the form of sulfide adversely interfers with both the dispersion and reducibility of the cobalt, so presulfiding should be avoided. Once the catalyst has been exposed to hydrocarbon for a sufficient period of time to lay down a protective layer of carbon or coke on the catalyst, the sulfur sensitivity of the catalyst changes rather markedly and the presence of small amounts of sulfur can be tolerated. Thus, contact of freshly reduced catalyst with sulfur can seriously damage the cobalt component and jeopardize the superior performance characteristics of the catalyst. However, once a protective layer of carbon is established on the catalyst, the sulfur deactivation effect is less permanent and the sulfur can be purged from the catalyst by exposure to a sulfur free hydrogen stream at 425° to 60° C.

According to the process of the present invention, an isomerizable hydrocarbon charge stock, preferably in admixture with hydrogen, is contacted with a catalyst of the type hereinbefore described in a hydrocarbon isomerization zone. Contacting may be effected using the catalyst in a fixed bed system, a moving bed system, a fluidized bed system, or in a batch type operation. In view of the danger of attrition loss of the valuable catalyst and of operational advantages it is preferred to use a fixed bed system. In this system, a hydrogen-rich gas and the charge stock are preheated by suitable heating means to the desired reaction temperature and then passed into an isomerization zone containing a fixed bed of the catalyst type previously characterized. The conversion zone may be one or more separate reactors with suitable means therebetween to insure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or a vapor phase when contacted with the catalyst, with best results obtained in a vapor phase.

The process of this invention, utilizing the catalyst described above for isomerizing isomerizable olefinic or saturated hydrocarbons, is preferably effected in a continuous down-flow fixed bed system. One preferred method is to pass the hydrocarbons continuously, preferably commingled with about 0.1 to about 10 moles or more of hydrogen per mole of hydrocarbon, to an isomerization reaction zone containing the catalyst, and to maintain the zone at proper isomerization conditions such as a temperature in the range of about 0° to about 425° C or more and a pressure of about atmospheric to about 100 atmospheres or more. The hydrocarbon is passed over the catalyst at a liquid hourly space velocity (defined as volume of liquid hydrocarbon passed per hour per volume of catalyst) of from about 0.1 to about 10 hr.$^{-1}$ or more. In addition, diluents such as argon, nitrogen, etc., may be present. The isomerized product is continuously withdrawn, separated from the reactor effluent, and recovered by conventional means such as fractional distillation, while the unreacted starting material may be recycled to form a portion of the feed stock.

The process of this invention for isomerizing an isomerizable alkylaromatic hydrocarbon is preferably effected by contacting the alkylaromatic, in a reaction zone containing the hereinbefore described catalyst, with a fixed catalyst bed by passing the hydrocarbon in a down-flow fashion through the bed, while maintaining the zone at proper alkylaromatic isomerization conditions such a a temperature in the range from about 0° C. to about 600° C. or more, and a pressure of atmospheric to about 100 atmospheres or more. The hydrocarbon is passed, preferably, in admixture with hydrogen at a hydrogen to hydrocarbon mole ratio of about 0.5:1 to about 20:1 or more, and at a liquid hourly hydrocarbon space velocity of about 0.1 to about 20 hr.$^{-1}$ or more. Other inert diluents such as nitrogen, argon, etc, may be present. The isomerized product is continuously withdrawn, separated from the reactor effluent by conventional means including fractional distillation or crystallization, and recovered.

The following illustrative embodiments are given to illustrate further the preparation of the trimetallic catalytic composite utilized in the process of the present invention and the employment of the catalyst in isomerization of hydrocarbons. It is to be understood that the examples are illustrative rather than restrictive.

ILLUSTRATIVE EMBODIMENT I

This example demonstrates a particularly good method of preparing the preferred catalytic composite utilized in the process of the present invention.

A tin-containing alumina carrier material comprising 1.6 mm spheres is prepared by: forming an aluminum hydroxyl chloride sol by dissolving substantially pure aluminum pellets in a hydrochloric acid solution, adding stannic chloride to the resulting sol in an amount selected to result in a finished catalyst containing 0.2 weight percent tin, adding hexamethylenetetramine to the resulting tin-containing alumina sol, gelling the resulting solution by dropping it into a hot oil bath to form spherical particles of an aluminum hydrogel containing tin in a particle size which is less than 100 Angstroms maximum chord length, aging and washing the resulting particles and finally drying and calcining the aged and washed particles to form spherical particles of gamma-alumina containing about 0.3 weight percent combined chloride and a uniform dispersion of about 0.2 weight percent tin in the form of tin oxide. Additional details as to this method of preparing the preferred carrier material are given in the teachings of U.S. Pat. No. 2,620,314.

An aqueous impregnation solution containing chloroplatinic acid, cobaltous chloride and hydrogen chloride is then prepared. This solution is then intimately admixed with the tin-containing gamma-alumina particles in amounts, respectively, calculated to result in a final composite containing, on an elemental base, 0.3 weight percent platinum, 1.0 weight percent cobalt and 0.2 weight percent tin. In order to insure uniform distribution of the metallic components throughout the carrier material, the amount of hydrogen chloride corresponds to about 3 weight percent of the alumina particles. This impregnation step is performed by adding the carrier material particles to the impregnation mixture with constant agitation. In addition, the volume of the solution is approximately the same as the void volume of the carrier material particles. The impregnation mixture is maintained in contact with the carrier material particles for a period of about one-half hour at a temperature of about 20° C. Thereafter, the temperature of the impregnation mixture is raised to about 106° C and the excess solution is evaporated in a period of about 1 hour. The resulting dried particles are then subjected to a calcination treatment in an air atmosphere at a temperature of about 495° C for about 1 hour. The calcined spheres are then contacted with an air stream containing $H_2O$ and HCl in a mole ratio of about 30.1 for about 2 hours at 525° C in order to adjust the halogen content of the catalyst particles to a value of about 1.09 weight percent.

The resulting catalyst particles are analyzed and found to contain, on an elemental basis, about 0.3 weight percent platinum, about 1.0 weight percent cobalt, about 0.2 weight percent tin and about 1.09 weight percent chloride. For this catalyst, the atomic ratio of tin to platinum is 1.1:1 and the atomic ratio of cobalt to platinum is 11:1.

Thereafter, the catalyst particles are subjected to a dry prereduction treatment designed to reduce the platinum and cobalt components to the elemental state while maintaining the tin component in a positive oxidation state by contacting them for one hour with a substantially pure hydrogen stream containing less than 5 vol. ppm. $H_2O$ at a temperature of about 565° C, a pressure slightly above atmospheric and a flow rate of the hydrogen stream through the catalyst particles corresponding to a gas hourly space velocity of about 720 $hr^{-1}$.

ILLUSTRATIVE EMBODIMENT II

A portion of the spherical trimetallic catalyst particles produced by the method described in Illustrative Embodiment I is loaded into a continuous, fixed bed isomerization plant of conventional design. The charge stock, containing on a weight percent basis, 20.0% ethylbenzene, 10.0% para-xylene, 50.0% meta-xylene, and 20.0% ortho-xylene is commingled with about 8 moles of hydrogen per mole of hydrocarbon, heated to 400° C, and continuously charged at 4.0 $hr^{-1}$ liquid hourly space velocity (LHSV) to the reactor which is maintained at a pressure of 30 atm absolute. The resulting product evidences essentially equilibrium conversion to para-xylene with only insignificant amounts of cracked products thus indicating an efficient alkylaromatic isomerization catalyst.

ILLUSTRATIVE EMBODIMENT III

A portion of the catalyst produced by the method of Illustrative Embodiment I is placed in a continuous flow, fixed bed isomerization plant of conventional design as utilized in Illustrative Embodiment II. Substantially pure meta-xylene is used as a charge stock. The charge stock is commingled with about 8 moles of hydrogen per mole of hydrocarbon, heated to about 390° C, and continuously charged to the reactor which is maintained at a pressure of about 21 atm. Substantial conversion of meta-xylene to para-xylene is obtained.

ILLUSTRATIVE EMBODIMENT IV

A catalyst identical to that produced in Illustrative Embodiment I but containing only 0.40 weight percent combined chloride is used to isomerize 1-butene in an appropriate isomerization reactor, at a reactor pressure of about 35 atm and a reactor temperature of about 140° C. Substantial conversion to 2-butene is observed.

ILLUSTRATIVE EMBODIMENT V

The same catalyst as utilized in Illustrative Embodiment IV is charged to an appropriate, continuous isomerization reaction of conventional design maintained at a reactor pressure of about 70 atm and a reactor temperature of about 180° C 3-methyl-1-butene is continuously passed to this reactor with substantial conversion to 2-methyl-2-butene being observed.

ILLUSTRATIVE EMBODIMENT VI

A catalyst, identical to that catalyst produced in Illustrative Embodiment I except that the gamma-alumina particles are contacted with hydrogen fluoride to provide a 2.9 weight percent combined fluoride content in the catalyst, is placed in an appropriate continuous isomerization reactor of conventional design maintained at a reactor pressure of about 21 atm psig, and a reactor temperature of about 200° C. Normal hexane is continuously charged to the reactor and substantial conversion to 2,2-dimethylbutane, 2,3-dimethylbutane, 2-methylpentane, and 3-methylpentane is observed.

ILLUSTRATIVE EMBODIMENT VII

A portion of the catalyst prepared in Illustrative Embodiment I is placed in an appropriate continuous isomerization apparatus and used to isomerize normal butane at a reactor pressure of 21 psig, a 0.5 hydrogen to hydrocarbon mole ratio, a 1.0 liquid hourly space velocity, and a reactor temperature of 230° C. Substantial conversion of normal butane to isobutane is observed.

ILLUSTRATIVE EMBODIMENT VIII

A portion of the catalyst prepared in Illustrative Embodiment I is placed in an appropriate continuous isomerization reactor maintained at a reactor temperature of about 210° C and a reactor pressure of about 18 atm. Methylcyclopentane is continuously passed to this reactor with a substantial conversion to cyclohexane being observed.

ILLUSTRATIVE EMBODIMENT IX

A sample of catalyst is prepared in a manner identical to that employed in Illustrative Embodiment I up to and including the calcination step. The calcined particles are then placed in a glass lined, rotating autoclave with anhydrous aluminum chloride. Three weights of $AlCl_3$ are added for each four weights of calcined particles. The autoclave is sealed, evacuated, then pressured with $H_2$ to 3 atm, absolute. The autoclave is heated to 300° C for 2 hours, with rotation. The calcined composite experienced a weight gain of 15 weight percent. These particles were then reduced in the manner disclosed in Illustrative Embodiment I.

ILLUSTRATIVE EMBODIMENT X

Catalyst prepared in Illustrative Embodiment IX is tested for isomerization of normal butane at a 0.5 $H_2$ to hydrocarbon ratio, 1.0 LHSV, and reactor temperature of 150° C. Substantial conversion of normal butane to isobutane is observed.

ILLUSTRATIVE EMBODIMENT XI

Catalyst is prepared as in Illustrative Embodiment I up to and including the calcination step. About 100 g of calcined particles are then placed in a vertical Pyrex tube with a bed of 30 g of AlCl$_3$ on top. H$_2$ at 250° C and gas hourly space velocity of 250 is passed over the bed until complete sublimation of AlCl$_3$ is observed. The temperature is then increased to 300° C for 30 minutes. The particles are then cooled under N$_2$ gas flow and reduced as described in Illustrative Embodiment I.

ILLUSTRATIVE EMBODIMENT XII

Catalyst prepared in Illustrative Embodiment XI is tested as disclosed in Illustrative Embodiment X. Substantial conversion of normal butane to isobutane is observed.

We claim as our invention:

1. A process for isomerizing an isomerizable naphthalene hydrocarbon selected from the group consisting of C$_5$ to C$_9$ naphthenes which comprises contacting said hydrocarbon at isomerization conditions with a catalyst comprising a porous carrier material containing, on an elemental basis, 0.01 to 2 wt. % platinum group metal, 0.1 to 5 wt. % cobalt, 0.01 to 5 wt. % tin and 0.1 to 10 wt. % halogen, wherein substantially all of the platinum group metal, cobalt and tin are uniformly dispersed throughout the porous carrier material, wherein substantially all of the platinum group metal and cobalt are present in the elemental metallic state and wherein substantially all of the tin is present in an oxidation state above that of the elemental metal.

2. Process of claim 1 wherein the tin has a particle size with a maximum chord length less than 100 Angstroms.

3. Process of claim 1 wherein the platinum group metal is selected from the group of platinum and palladium.

4. Process of claim 1 wherein the porous carrier material is a refractory inorganic oxide.

5. Process of claim 1 wherein the refractory inorganic oxide is alumina.

6. Process of claim 1 wherein the halogen is combined chloride.

7. Process of claim 1 wherein the atomic ratio of tin to platinum group metal is 0.1:1 to 13:1.

8. Process of claim 1 wherein the atomic ratio of cobalt to platinum group metal is 0.8:1 to 66:1.

9. Process of claim 1 wherein substantially all of the tin is present as tin oxide.

10. Process of claim 1 containing 0.05 to 1 wt. % platinum, 0.5 to 2 wt. % cobalt, 0.05 to 1 wt. % tin, 0.5 to 1.5 wt. % halogen.

11. Process of claim 1 wherein the catalyst contains, on an elemental metal basis, a total metals content of 0.15 to 5 wt. %.

12. Process of claim 1 wherein the catalytic composite additionally contains 1 to 100 wt. % of a Friedel-Crafts metal halide based on a Friedel-Crafts metal halide-free composite.

13. Process of claim 1 wherein the Friedel-Crafts metal halide is aluminum chloride.

14. Process of claim 1 wherein the isomerization conditions include a temperature of 0° to 425° C., a pressure of atmospheric to 100 atmospheres, and a liquid hourly space velocity of 0.1 to 10.

15. Process of claim 1 wherein the naphthene hydrocarbon is commingled with 0.1 to 10 moles of hydrogen per mole of hydrocarbon.

* * * * *